United States Patent [19]

Garrett

[11] Patent Number: 5,392,782
[45] Date of Patent: Feb. 28, 1995

[54] DISPOSABLE MEDICAL PRESSURE CUFFS AND METHOD OF PRODUCTION

[76] Inventor: John R. Garrett, 37 Pine Arbor #204, Vero Beach, Fla. 32962

[21] Appl. No.: 192,543

[22] Filed: Feb. 7, 1994

[51] Int. Cl.⁶ .............................................. A61B 5/022
[52] U.S. Cl. .................................... 128/686; 606/202
[58] Field of Search .................. 128/686; 606/201–203

[56] References Cited

U.S. PATENT DOCUMENTS

| | | | |
|---|---|---|---|
| 3,570,495 | 3/1971 | Wright | 606/202 |
| 3,603,304 | 9/1971 | Maier | 128/686 |
| 4,635,635 | 1/1987 | Robinette-Lehman | 606/202 |
| 5,179,957 | 1/1993 | Williams | 606/202 X |
| 5,193,549 | 3/1993 | Bellin et al. | 606/202 X |

FOREIGN PATENT DOCUMENTS 1068749  5/1967  United Kingdom ................ 128/686

Primary Examiner—Angela D. Sykes
Attorney, Agent, or Firm—Carroll F. Palmer

[57] ABSTRACT

Disposable medical pressure cuffs of the type having one side made from a flexible non-porous plastic sheet and the other side made from a woven fabric sheet that presents a fleecy surface to provide comfort when in contact with the body of a patient are improved to prevent air leakage around joints of such sheets with inflation fittings by containing them in a small, fabric sheet-free section along the longitudinal edge of the cuff where the fittings enter the cuff and flanges of the fittings are heat sealed to the inside surface of the plastic sheet within the area of such section. Methods for forming such improved cuff structures are disclosed.

7 Claims, 3 Drawing Sheets

DISPOSABLE MEDICAL PRESSURE CUFFS AND METHOD OF PRODUCTION

BACKGROUND OF THE INVENTION

1. Field of the Invention

This application relates broadly to improved disposable medical pressure cuffs, particularly disposable, blood pressure measurement cuffs. It also concerns new methods for their production.

2. Description of the Prior Art

Flexible, inflatable pressure cuffs that can be wrapped about the arm or other body portion of a person or animal for measurement of blood pressure or as a tourniquet have been in existence for decades. Historically, such cuffs were of a permanent type that would be used by a physician or at a bed station in a hospital until they wore out and had to be replaced.

It has been long recognized that such cuffs constitute a potential source of cross-infection between patients. As a result, substantial work has been devoted to the development of structural arrangements and production methods seeking to provide medical pressure cuffs that are reliable for use in medical practice, but that can be made and sold at such a low a cost they can be treated as disposable items permitting them to be used on a single patient and then discarded, e.g., see U.S. Pat. Nos. 4,979,953; 5,101,830 and 5,193,549.

The earliest style of disposable pressure cuffs were formed from a single sheet of flexible, heat sealable plastic such as plasticized polyvinyl chloride or polyurethane with one or two small holes punched in a central area in which flanged inflation fittings are inserted and heat sealed by their flanges to the material. This sheet was then folded in half and its perimeter edges were sealed together with dielectric heat (RF heat sealing) to form the completed cuff. Small amounts of hook and loop fasteners are attached to the cuff by RF heat sealing or pressure sensitive adhesive so as to enable the cuff to be secured to a patient's limb.

This early style of disposable cuffs proved easy to manufacture, were reliable and offered the advantage of the plasticized material being easily cleaned. The plasticized material, however, proved to be uncomfortable to patients because of the clammy feeling presented by the plastic films in contact with the patients. Further, the plastic films on the patient's skin caused perspiration and provided a nutritive environment for bacteria growth. Accordingly, a second style of disposable cuffs was developed in which a non-clammy type fabric would contact the patient when the cuff was in the operative position.

Such second style cuffs are typically made in two different ways. In a first way, the cuff is formed by a single laminate sheet having an outside layer of soft fabric and an inside layer of plastic or elastomer (see U.S. Pat. No. 5,193,549) with one or two holes punched in a central area to which flanged inflation fittings are RF sealed. The sheet is then folded in half and its perimeter edges sealed together to form a completed cuff.

In a second way, the cuff is formed of one sheet of flexible plastic and a second separate, equal size piece of soft fabric with a plasticized backing, with the two sheets laid in contact with each other. One or two small inlet (inflation) tubes are laid side by side at one longitudinal edge and between the two sheets. A small, special RF die is used to seal the sheets about and around the inlet tubes and the cuff is then completed by RF sealing of the perimeter of the plastic and fabric sheets.

Both of the ways described above have advantages and disadvantages. In the first way, because the method of manufacturing allows flanged inflation fittings to be RF sealed, this results in leak free operation. The soft fabric materials that are used also provide the patient with increased comfort. However, such materials are much more expensive than plastic materials and are much more difficult to clean. The second way still provides the soft material next to the patient's skin, yet reduces material expense by using a plasticized material on the other side. However, this second way involves a disadvantage since the 360 degree seal around the inlet tubes is difficult to make so that there will be no leaks. Hence, most air leakage in disposable cuffs using this method occurs around the inlet tubes. The process also requires much more expensive equipment and sealing dies.

OBJECTS

A principal object of the invention is the provision of improved disposable medical pressure cuffs, particularly disposable blood pressure measurement cuffs.

Further objects include the provision of:

1. New methods for the production of disposable medical pressure cuffs.
2. Disposable medical pressure cuffs made of a first sheet of flexible plastic heat sealed at the perimeter to a second sheet of fabric presenting a comfortable, patient contact surface and which have a unique installation of flanged inflation fittings that eliminate any air leakage problem associated with prior art cuffs that use two different types of material, i.e., plastic and soft fabric.

Other objects and further scope of applicability of the present invention will become apparent from the detailed descriptions given herein; it should be understood, however, that the detailed descriptions, while indicating preferred embodiments of the invention, are given by way of illustration only, since various changes and modifications within the spirit and scope of the invention will become apparent from such descriptions.

SUMMARY OF THE INVENTION

The objects are accomplished in accordance with the invention, in part, by the provision of a disposable medical pressure cuff comprising a first flexible sheet of plastic material and a second flexible sheet comprising a woven fabric, the first and second sheets being held together by perimeter heat sealing.

The flexible first sheet is made of plastic, e.g., polyvinyl chloride, polyurethane or the like. Such sheet is die cut into a generally rectangularly shape presenting a first straight longitudinal edge, a pair of second and third straight transverse edges of equal length less than the first edge and a fourth longitudinal edge that includes a short length tab section.

The flexible second sheet comprises a woven fabric defined by a fleecy outside surface, an air impervious inside surface, a first straight longitudinal edge, a pair of second and third straight transverse edges of equal length less than the first edge and a fourth longitudinal edge that includes a short length indent section positioned and sized so that it mates with and overlaps the first sheet except for a portion only of the tab section of the first sheet.

The fleecy outside surface of the second sheet is advantageously loop fabric of the type used in loop/hook type flexible fastening arrangements as exemplified by Velcro ®.

The tab section of the first sheet has at least one flanged inflation fitting extending through a hole therein sealed by its flange to the inside surface of the first sheet and the outside surface of the perimeter of the tab is sealed to the inside surface of the perimeter of the indent section of the second sheet.

In a first embodiment, the periphery of the inside surface of the first sheet is heat sealed to the periphery of the inside surface of the second sheet along the first, second, third, and fourth edges thereof forming an inflatable compartment between the first and second sheets.

In a second embodiment, the periphery of the outside surface of the first sheet is heat sealed to the outside surface of the second sheet along their first, second, and third edges while the periphery of the inside surface of the first sheet is heat sealed to the inside surface of the second sheet along their fourth edges thereby forming an inflatable compartment between the first and second sheets.

The objects of the invention are further attained by a method for production of disposable medical pressure cuffs that comprises the steps of (a) providing a flexible first sheet made of plastic defined by a smooth inside surface, a smooth outside surface, a first straight longitudinal edge, a pair of second and third straight transverse edges of equal length less than the first edge and a fourth longitudinal edge that includes a short length tab section positioned between the transverse edges with the tab section having at least one hole therein, (b) providing a flexible second sheet comprising a woven fabric defined by a fleecy outside surface, an air impervious inside surface, a first straight longitudinal edge, a pair of second and third straight transverse edges of equal length less than the first edge and a fourth longitudinal edge that includes a short length indent section positioned and sized to overlap a portion only of the tab section of the first sheet, (c) positioning the first sheet with its inside surface face up and its fourth edge, but not overlapping, the fourth edge of the second sheet, positioned inside surface facing up, and with the periphery of the outside surface of the tab section of the first sheet overlapping the periphery of the inside surface of the indent section of the second sheet, (d) extending a flanged inflation fitting through each hole in the tab and heat sealing the flanged inflation fitting to the inside surface of the first sheet at the same time as the overlapping peripheries of the tab and indent are sealed together, (f) folding the first sheet relative to the second sheet so their inside surfaces face each other with their first, second, third and fourth edges aligned, and (g) heat sealing the inside surface of the first sheet to the inside surface of the second sheet along the first, second, third and fourth edges thereof forming an inflatable compartment between the first and second sheets.

In a second embodiment of the new methods, the outside surface of the fourth edge of the first sheet overlaps the inside edge of the fourth edge of the second sheet when the first sheet tab and second sheet indent are overlapped and such overlapped fourth edges are heat sealed together at the same time the tab and indent are heat sealed. Then the first sheet is bent over the second sheet so their inside surfaces face each other and the peripheries of their first, second and third edges are heat sealed together to form an inflatable compartment between them.

BRIEF DESCRIPTION OF THE DRAWINGS

A more complete understanding of the invention can be obtained by reference to the accompanying drawings in which.

DESCRIPTION OF THE PREFERRED EMBODIMENTS

Figure 1:
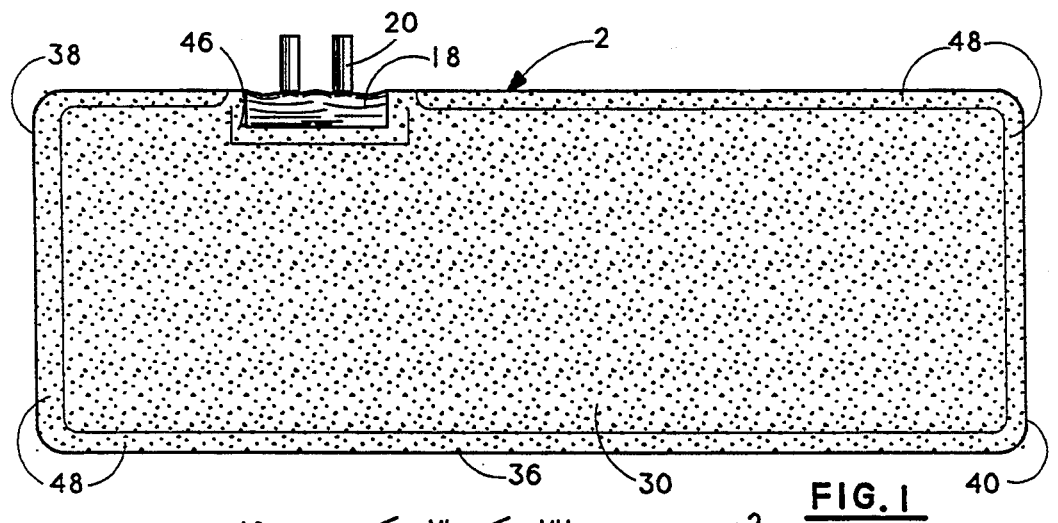
FIG. 1 is a plan view of an improved disposable medical pressure cuff of the invention from the side which contacts the patient during use.
Figure 2:
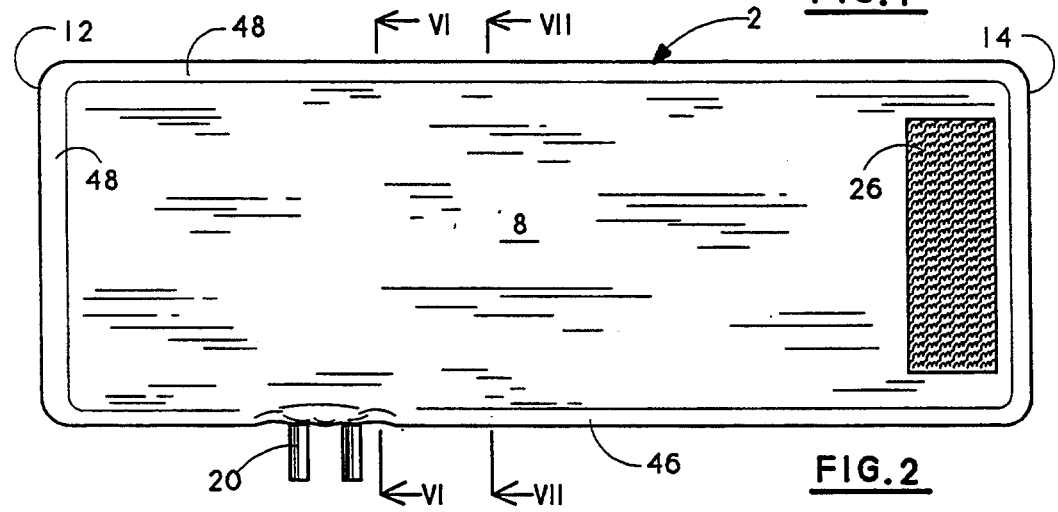
FIG. 2 is a plan view of the reverse side of the pressure cuff of FIG. 1 with a hook component of a hook/loop type fastener adhered to one end.
Figure 3:
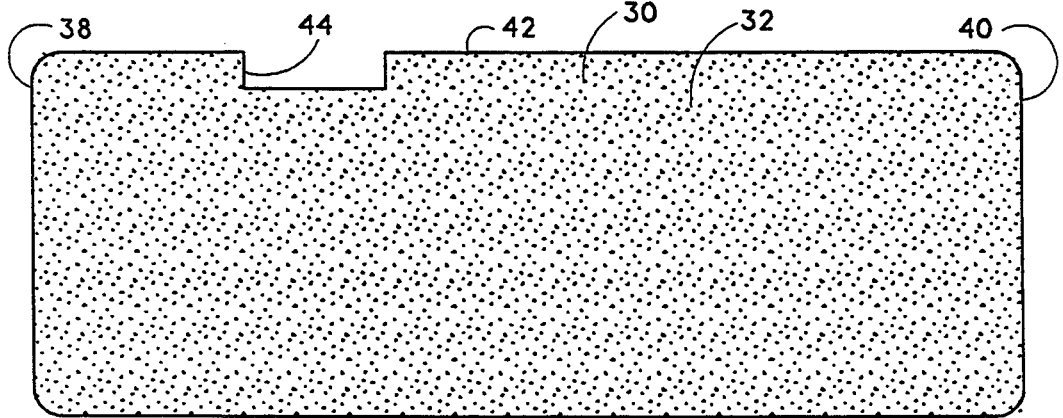
FIG. 3 is a plan view of a sheet of a fleece fabric die cut to shape for forming a pressure cuff as shown in FIGS. 1 & 2.
Figure 8:
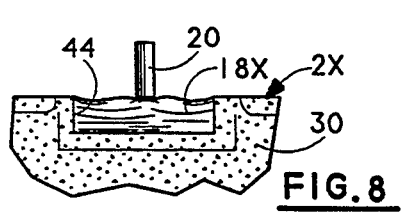
FIG. 8 is a fragmentary plan view of a second embodiment of a pressure cuff of the invention.
Figure 9:
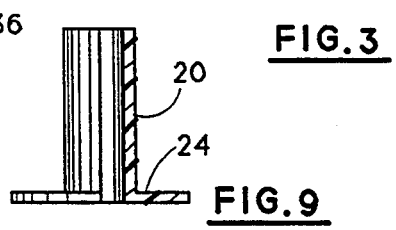
FIG. 9 is an enlarged, lateral view, one half sectioned, of a flanged fitting used in the construction of pressure cuffs of the invention.
Figure 4:
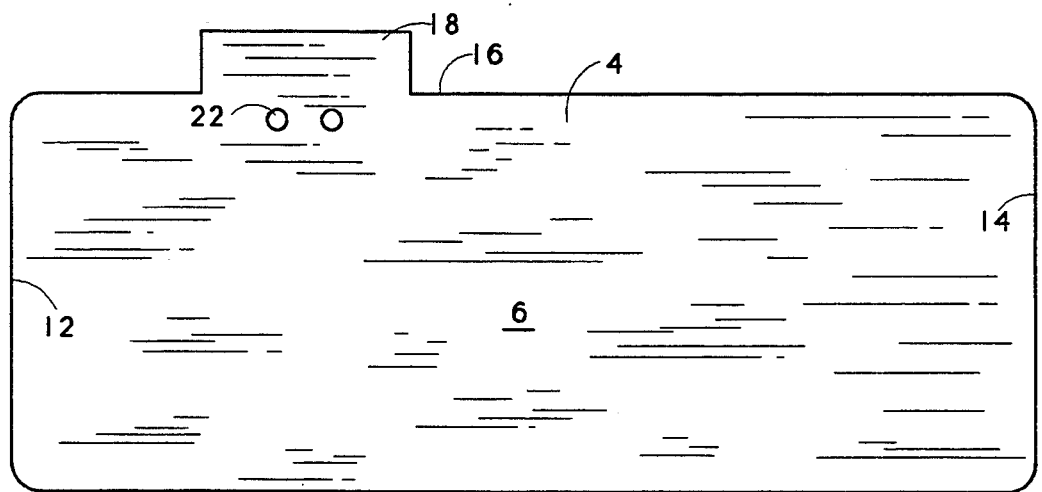
FIG. 4 is a plan view of a flexible sheet of flexible plastic die cut to shape for forming a pressure cuff as shown in FIGS. 1 & 2.

Referring in detail to the drawings, a disposable medical pressure cuff 2 of the invention comprises a flexible first sheet 4 made of plastic which has an inside surface 6, a outside surface 8 and has been die cut to have a first straight longitudinal edge 10, a pair of second and third straight transverse edges 12 & 14 and a fourth longitudinal edge 16 that includes a short length tab section 18. The corners of sheet 4 are filleted.

The tab section 18 has a pair of flanged inflation fittings 20 extending through holes 22 therein that are heat sealed by their flanges 24 to the inside surface 6 of the first sheet 4.

A hook component 26 of a hook/loop type fastener is attached to outside surface 8 at any suitable location, e.g., adjacent transverse edge 14.

The cuff 2 further includes a flexible second sheet 30 of woven fabric having a fleecy outside surface 32 and an air impervious inside surface 34. The sheet 30 is die cut to present a first straight longitudinal edge 36, a pair of second and third straight transverse edges 38, 40 and a fourth longitudinal edge 42 that includes a short length indent section 44. The corners of sheet 30 are filleted.

Figure 5:
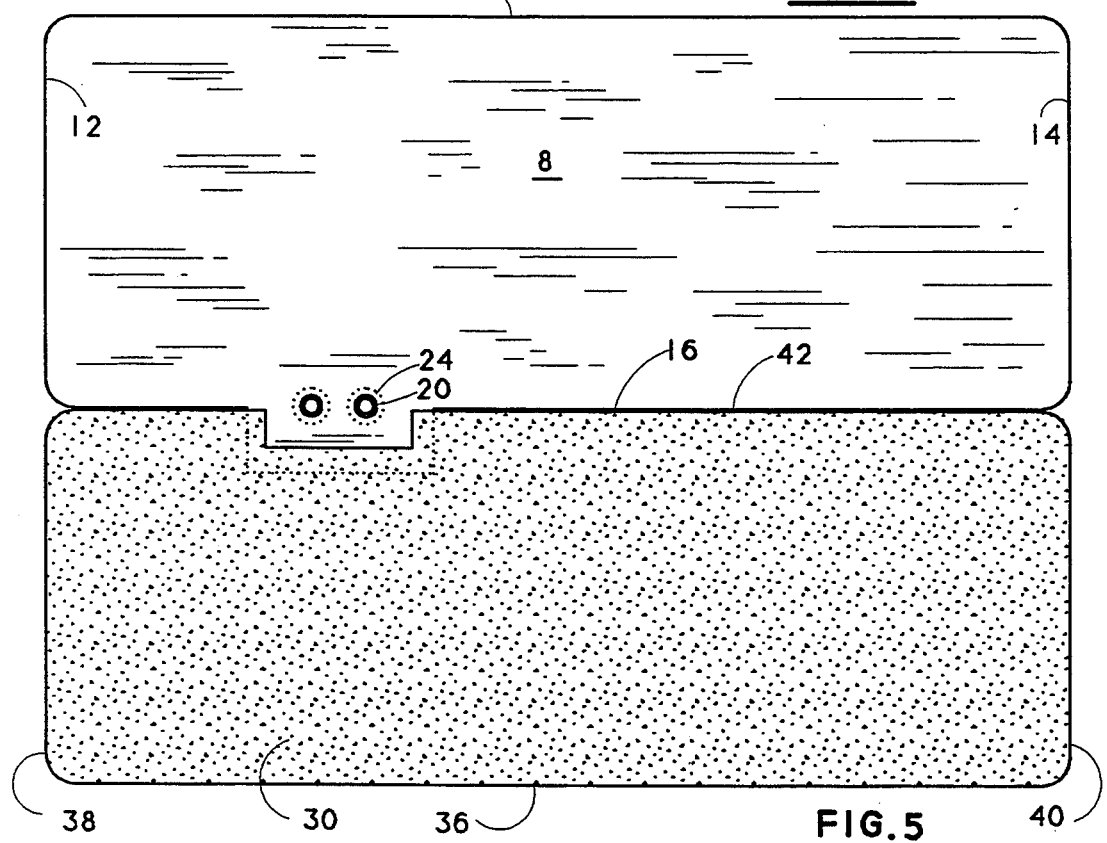
FIG. 5 is a plan view of the sheets of FIGS. 3 & 4 in one stage of assembly to form a pressure cuff as shown in FIGS. 1 & 2.
Figure 6:
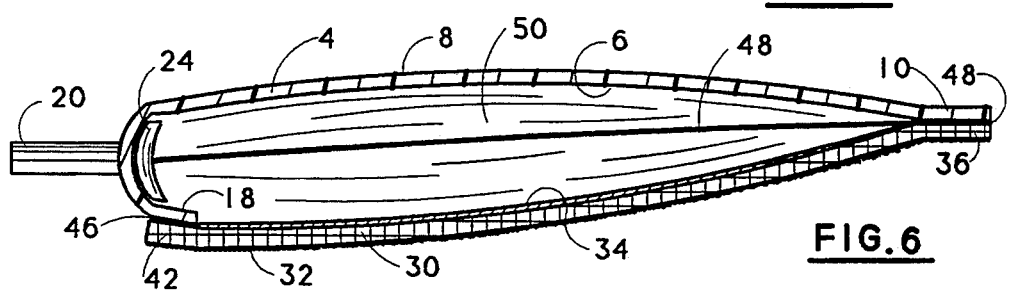
FIG. 6 is an enlarged sectional view taken on the line VI—VI of FIG. 2.

As seen in FIG. 5, the inside surface 34 of the periphery of the indent 44 of sheet 30 overlaps and is attached by heat seal 46 to the outside surface 8 of the periphery of the tab 18 of sheet 4.

The inside surface 6 of sheet 4 is fixed by heat seal 48 to the inside surface 34 of second sheet 30 along the first, second, third and fourth edges 36, 38, 40 & 42 respectfully forming an inflatable compartment 50 between the sheets 4 & 30.

Figure 7:
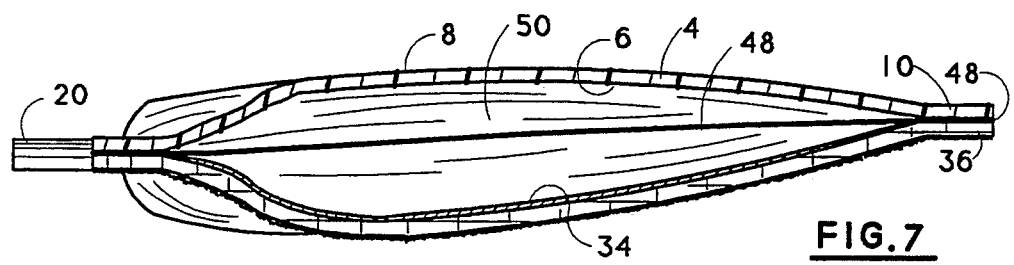
FIG. 7 is an enlarged sectional view taken on the line VII—VII of FIG. 2.

In the embodiment of the pressure cuff 2X as shown in FIG. 7, a single flanged fitting 20 is heat sealed to the tab section 18X of the cuff 2X. Some pressure monitoring systems (not shown) used with medical pressure cuffs require only one inlet into inflatable cuffs while others require two inlets. Hence, the two embodiments shown and described are supplied to meet the demands of a variety of monitoring systems.

Figure 10:
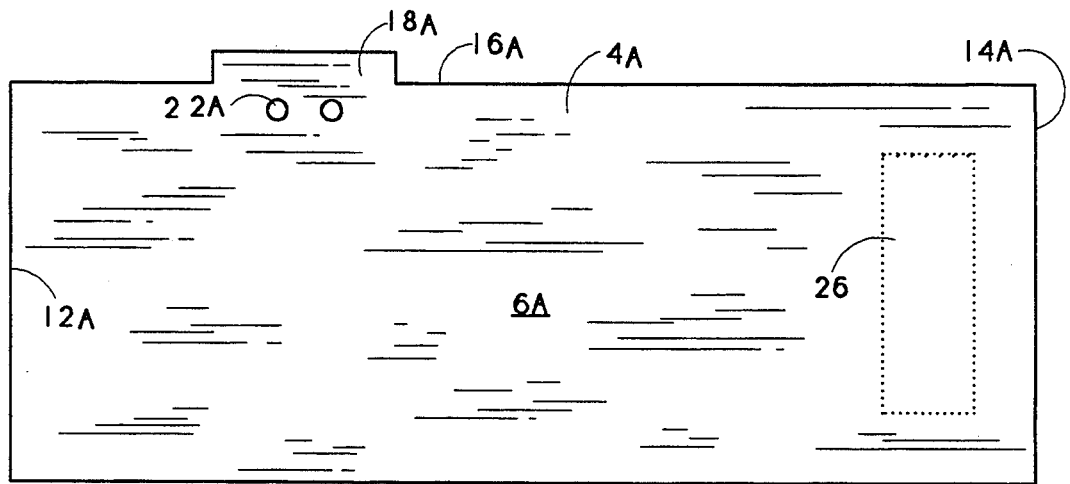
FIG. 10 is a plan view of another flexible sheet of flexible plastic die cut to shape for forming a pressure cuff in accordance with the invention.
Figure 11:
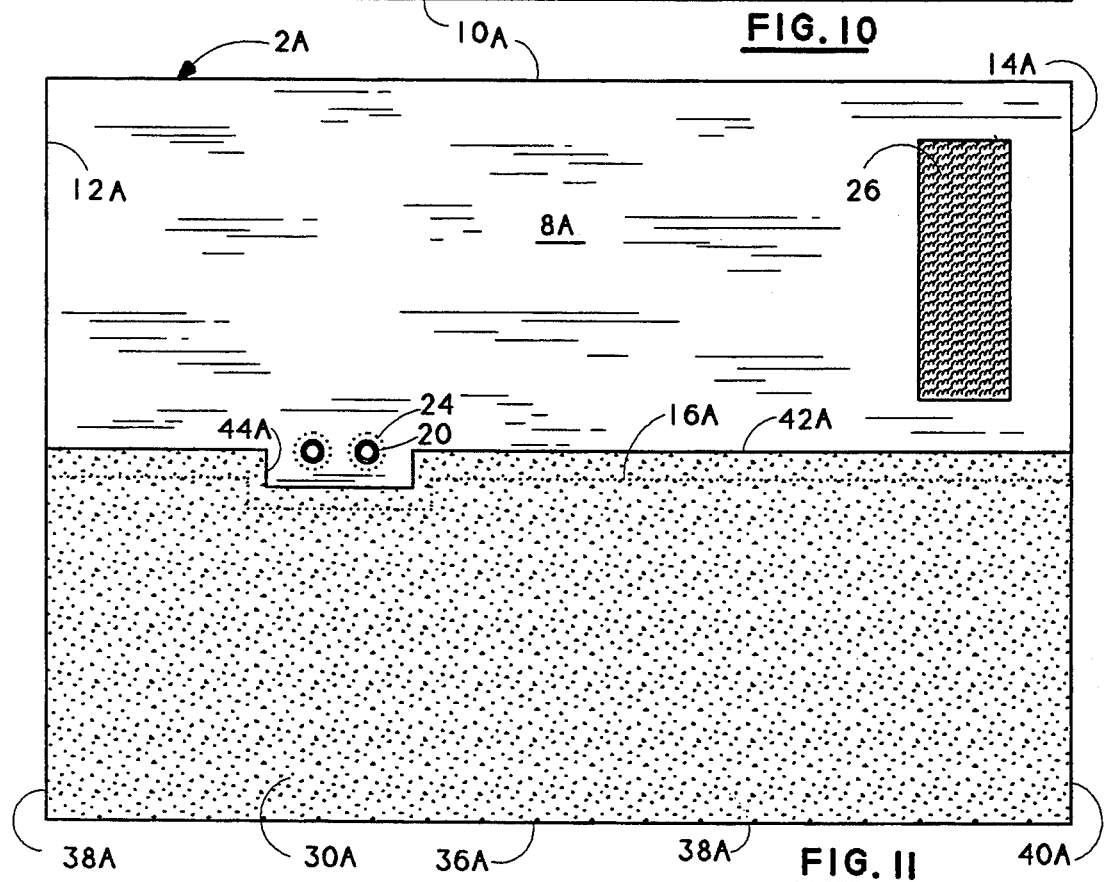
FIG. 11 is a plan view of the sheet of FIGS. 10 positioned with a sheet of a fleece fabric die cut to shape for forming a pressure cuff in one stage of their assembly to form a pressure cuff in accordance with the invention.

In the embodiment of the pressure cuff 2A as shown in FIGS. 10 & 11, the fourth edge 16A of the outside surface 8A of sheet 4A overlaps the fourth edge 42A of the inside surface of second sheet 30A and these are heat sealed together at the same time that tab 18A is heat sealed to the overlapped portion of the indent portion 44A of sheet 30A. Also, in the finished cuff 2A (not shown), the inside surface 6A of sheet 4A is fixed by a heat seal to the inside surface 34A of second sheet 30A along the first, second and third edges 36A, 38A & 40A respectfully forming an inflatable compartment (not shown) between the sheets 4A & 30A.

The production of the first embodiment disposable medical pressure cuffs 2 & 2X in accordance with the invention may be fully understood by reference to FIGS. 3-6.

A first step is the provision of a first sheet 4 by die cutting it from a supply roll of flexible plastic (not shown) to have a shape as shown defined by a first straight longitudinal edge 10, a pair of second and third straight transverse edges 12 & 14 and a fourth longitudinal edge 16 that includes a short length tab section 18 having at least one hole 22 therein.

In a second step, a flexible second sheet 30 is provided by die cutting a woven fabric having a fleecy outside surface 32 and air impervious inside surface 34 from a roll thereof (not shown) to have a first straight longitudinal edge 36, a pair of second and third straight transverse edges 38 & 40 and a fourth longitudinal edge 42 that includes a short length indent section 44 as shown.

In a third step, the fourth edge 16 sheet 4 is positioned as shown in FIG. 5 adjacent to and aligned with the fourth edge 42 of sheet 30 with the indent section 44 overlapping the tab section 18.

In a fourth step, a flanged fitting 20 is extended through each hole 22 in the tab section 18 and is heat sealed by its flange 24 to the inside surface 6 of sheet 4. At the same time, the overlapped portions of the tab 18 and the indent 44 are sealed together.

In a fifth step, sheets 4 and 30 are folded relative to each other so their inside surfaces 6 & 34 respectively face each other and their respective first, second, third and fourth edges are aligned.

In a sixth step, the inside surface 6 of sheet 4 is fixed by heat seals 48 to the inside surface 34 of sheet 30 along the first, second, third and fourth edges thereof forming an inflatable compartment 50 between the sheets 4 & 30.

As a final step, a hook component 26 is attached via its pressure sensitive adhesive backing to surface 8 of sheet 4. Alternatively, component 26 sans PS adhesive can be heat sealed to sheet 4 during one of the prior steps.

The production of the second embodiment disposable medical pressure cuffs 2A in accordance with the invention may be fully understood by reference to FIGS. 10 & 11.

A first step is the provision of a first sheet 4A by die cutting it from a supply roll of flexible plastic (not shown) to have a shape as shown defined by a first straight longitudinal edge 10A, a pair of second and third straight transverse edges 12A & 14A and a fourth longitudinal edge 16A that includes a short length tab section 18A having at least one hole 22A therein. At this time or at any subsequent step, the hook component 26 may be attached.

In a second step, a flexible second sheet 30A is provided by die cutting a woven fabric having a fleecy outside surface 32A and air impervious inside surface 34A from a roll thereof (not shown) to have a first straight longitudinal edge 36A, a pair of second and third straight transverse edges 38A & 40A and a fourth longitudinal edge 42A that includes a short length indent section 44A as shown.

In a third step, the fourth edge 16A of the outside surface 8A of sheet 4A is positioned as shown in FIG. 5 in overlapping contact with the fourth edge 42A of the inside surface 34A of second sheet 30A with the indent section 44A overlapping the tab section 18A.

In a fourth step, a flanged fitting 20 is extended through each hole 22A in the tab section 18A and is heat sealed by its flange 24 to the inside surface 6A of sheet 4A at the same time as the overlapped portions of edge 16A, edge 42A, the tab 18A and the indent 44A are sealed together.

In a fifth step, sheet 4A and sheet 30A are folded relative to each other so their inside surfaces 6A & 34A respectively face each other and their respective edges 10A, 12A, 14A, 36A, 38A and 404 are aligned.

In a sixth step, the inside surface 6 of sheet 4 is heat sealed to the inside surface 34 of sheet 30 along the aligned edges thereof forming an inflatable compartment (not shown) between the first and second sheets.

The embodiments of the invention in which an exclusive property or privilege is claimed are defined as follows:

1. A disposable medical pressure cuff comprising:
   a flexible first sheet made of plastic defined by an inside surface, an outside surface, a first straight longitudinal edge, a pair of second and third straight transverse edges of equal length less than said first edge and a fourth longitudinal edge that includes a short length tab section positioned between said transverse edges,
   said tab section having at least one flanged fitting extending through a hole in said tab section and heat sealed by its flange to said inside surface of said first sheet,
   a flexible second sheet comprising a woven fabric defined by a fleecy outside surface, an air impervious inside surface, a first straight longitudinal edge, a pair of second and third straight transverse edges of equal length less than said first edge and a fourth longitudinal edge that includes a short length indent section positioned and sized so its peripheral area only overlaps a portion only of said tab section of said first sheet,
   the outside surface of said first sheet defined by said portion of said tab section being heat sealed to said inside surface of said second sheet defined by said peripheral area of said indent section, and
   said first sheet being heat sealed to said second sheet along said first, second, third and fourth edges thereof forming an inflatable compartment between said first and second sheets.

2. The disposable medical pressure cuff of claim 1 that has a pair of holes in said tab section and flanged nipples extending through said holes and said nipples being heat sealed by their flanges to said inside surface of said first sheet.

3. The disposable medical pressure cuff of claim 1 that includes a section of a hook component of a hook/loop fastener attached to said outside surface of said first sheet.

4. A method for production of disposable medical pressure cuffs that comprises:
providing a flexible first sheet made of plastic defined by an inside surface, an outside surface, a first straight longitudinal edge, a pair of second and third straight transverse edges of equal length less than said first edge and a fourth longitudinal edge that includes a short length tab section positioned between said transverse edges, said tab section having at least one hole therein,
providing a flexible second sheet comprising a woven fabric defined by a fleecy outside surface, an air impervious inside surface, a first straight longitudinal edge, a pair of second and third straight transverse edges of equal length less than said first edge and a fourth longitudinal edge that includes a short length indent section positioned and sized to overlap a portion only of said tab section of said first sheet,
positioning said fourth edge of said first sheet along said fourth edge of said second sheet so said indent section overlaps said tab section,
extending a flanged fitting through each hole in said tab section and heat sealing said fitting by its flange to said inside surface of said first sheet while also heat sealing said indent section to said tab section,
heat sealing said fourth edge of said first sheet to said fourth edge of said second sheet, and
heat sealing said inside surface of said first sheet to said inside surface of said second sheet along said first, second and third edges thereof forming an inflatable compartment between said first and second sheets.

5. The method of claim 4 including providing a pair of holes in said tab section, extending said flanged nipples through said holes and heat sealing said nipples by their flanges to said inside surface of said first sheet.

6. The method of claim 4 including fixing a section of a hook component of a hook/loop fastener to said outside surface of said first sheet.

7. A method for production of disposable medical pressure cuffs that comprises:
providing a flexible rectangular first sheet made of plastic defined by an inside surface, an outside surface, a first straight longitudinal edge, a pair of second and third straight transverse edges of equal length less than said first edge and a fourth longitudinal edge that includes a short length tab section positioned between said transverse edges, said tab section having at least one hole therein,
providing a flexible rectangular second sheet comprising a woven fabric defined by a fleecy outside surface, an air impervious inside surface, a first straight longitudinal edge, a pair of second and third straight transverse edges of equal length less than said first edge and a fourth longitudinal edge that includes a short length indent section positioned and sized to overlap a portion only of said tab section of said first sheet,
positioning said first sheet with its said outside surface face up and its said fourth edge juxtaposed to said fourth edge of said second sheet with its said outside surface face up and said indent section of said second sheet overlapping said tab section of said first sheet,
extending a flanged fitting through each hole in said tab section and heat sealing said fitting by its flange to said inside surface of said first sheet while also heat sealing said indent section to said tab section,
folding said first sheet relative to said second sheet so their said inside surfaces face each other with their first, second, third and fourth edges aligned,
heat sealing said inside surface of said first sheet to said inside surface of said second sheet along said first, second, third and fourth edges thereof forming an inflatable compartment between said first and second sheets, and
attaching a section of a hook component of a hook/loop type fastener to said outside surface of said first sheet.

* * * * *